(12) United States Patent
Moos et al.

(10) Patent No.: US 6,463,789 B2
(45) Date of Patent: Oct. 15, 2002

(54) GAS SENSOR

(75) Inventors: Ralf Moos, Friedrichshafen; Thomas Birkhofer, Immenstaad; Aleksandar Knezevic, Kirchheim/Teck; Ralf Mueller, Aulendorf; Carsten Plog, Markdorf, all of (DE)

(73) Assignee: Dornier GmbH, Friedrichshafen (DE)

( * ) Notice: Subject to any disclaimer, the term of this patent is extended or adjusted under 35 U.S.C. 154(b) by 0 days.

(21) Appl. No.: 09/801,675

(22) Filed: Mar. 9, 2001

(65) Prior Publication Data
US 2001/0020383 A1 Sep. 13, 2001

(30) Foreign Application Priority Data
Mar. 9, 2000 (DE) .......................................... 100 11 562

(51) Int. Cl.$^7$ ........................... G01N 27/14; G01N 7/00; G01N 27/12
(52) U.S. Cl. ..................... 73/31.06; 73/31.05; 324/609; 422/98
(58) Field of Search ............................. 73/31.06, 31.05, 73/23.2; 422/82.01, 82.02, 98; 324/609

(56) References Cited

U.S. PATENT DOCUMENTS

| | | | | |
|---|---|---|---|---|
| 4,580,439 A | * | 4/1986 | Manaka | 73/23 |
| 4,706,493 A | * | 11/1987 | Chang et al. | 73/23 |
| 5,250,170 A | * | 10/1993 | Yagawara et al. | 204/431 |
| 5,786,608 A | * | 7/1998 | Lescouzeres et al. | 257/253 |
| 5,866,800 A | * | 2/1999 | Park et al. | 73/31.06 |
| 5,879,630 A | * | 3/1999 | Lescouzeres et al. | 422/82.02 |
| 5,918,261 A | * | 6/1999 | Williams et al. | 73/31.06 |
| 6,114,943 A | * | 9/2000 | Lauf | 338/34 |
| 6,161,421 A | * | 12/2000 | Fang et al. | 73/31.05 |
| 6,265,222 B1 | * | 7/2001 | DiMeo, Jr. et al. | 436/144 |
| 6,298,710 B1 | * | 10/2001 | Sammon et al. | 73/31.06 |

FOREIGN PATENT DOCUMENTS

DE 198 33 453 2/2000

* cited by examiner

Primary Examiner—Hezron Williams
Assistant Examiner—David J. Wiggins
(74) Attorney, Agent, or Firm—Crowell & Moring LLP

(57) ABSTRACT

A gas sensor, comprises a substrate, a sensor unit including a functional layer and an electrode structure, and an electric heating and/or temperature measuring arrangement. An electrically conductive shielding structure is provided between the sensor unit and the electric heating arrangement in order to shield the measurement process at the sensor unit from interferences owing to the heating process, thereby reducing or preventing the effects of electrical fields caused by voltages applied to the heating arrangement from altering or disrupting the measurement process.

12 Claims, 12 Drawing Sheets

GAS SENSOR

BACKGROUND AND SUMMARY OF THE INVENTION

This application claims the priority of German patent document 100 11 562.4, filed Mar. 9, 2000, the disclosure of which is expressly incorporated by reference herein.

The invention relates to a gas sensor having functional layer and an electrode structure mounted on a substrate, with an electric heater.

More exacting requirements for environmental protection and air quality demand both engineering solutions to improve the air quality, and measures for monitoring the air quality. For cost reasons it is desirable to avoid the use of expensive gas analysis equipment, and, instead, to use small gas sensors, which are inexpensive to produce, as the detectors for the air quality. One application, where the most exacting requirements for long service life and immunity to interference under the rawest surrounding atmospheres are demanded, is the exhaust gas of an automobile. In this respect very special sensors, which select specific gases, are required for varying drive concepts.

Such gas sensors, which are usually operated at temperatures in the range of several hundred degrees Celsius, can be produced inexpensively by means of planar technology and generally exhibit a layout as described in FIG. 1. A heater and/or a temperature measuring device 4 in the form of a resistance thermometer is/are applied on the sensor bottom side of a transducer, which generally includes an electrically insulating substrate 1. The heater and/or temperature measuring device has leads, which are supposed to exhibit minimum lead resistance (labeled $R_{lead}$ in FIG. 4), and comprise(s) a heating and temperature measuring structure ($R_{heating}$ in FIG. 4) that frequently has a meandering shape. An electrode structure 6, which is adapted to the special requirements, is then applied on the upper side of the sensor. On the electrode structure is applied a functional layer 7, which determines the special properties of the sensor, such as the selectivity for a specific gas, etc. This functional layer changes its electrical properties as a function of the composition of the gas atmosphere surrounding the sensor. At the sensor tip a constant temperature is supposed to prevail on the sensor upper side in the area where the functional layer is applied. The constant temperature is adjusted to a specific temperature, the so-called working temperature, by means of the heating and temperature probe on the sensor bottom side.

The ambient atmosphere-dependent electric properties of the functional layer are called the measured variable in the following. For example, it can be: the complex impedance Z or derived variables, such as the capacitance, the loss resistance, the phase angle or the magnitude of the complex impedance. In the case of a measuring frequency of 0 Hz (d.c. voltage) the direct current resistance must also be defined as the measured variable. In the case of a highly resistive functional layer, an interdigitated capacitor structure (IDC) is used as the electrode structure, as sketched in Plog C., Maunz W., Kurzweil P., Obermeier E., Scheibe C.: Combustion Gas Sensitivity of Zeolite Layers on Thin Film Capacitors. "Sensors and Actuators", B 24–25, (1995), 403–406 and in German patent documents DE 19703796, EP 0527259 or DE 19635977. In the case of highly conductive samples, an electrode arrangement with large electrode intervals is best provided, such as in the German patent document DE 19744316, where a four conductor arrangement was selected as the electrode arrangement for a semiconducting titanate as the functional layer.

However, the measured variable can also be an electromotive force (EMF) between two electrodes, e.g., of an ionic conductor. Thermoelectric voltages can also be a measured variable. In the case of a limiting current sensor the current that flows when a voltage U is applied, is a function of the measuring gas concentration and thus the measured variable.

Typical gas sensors, which are constructed according to the above pattern, can be derived from the following documents. European patent document EP 0426989 presents a selective HC sensor, whose capacitance changes with the gas test. German patent document DE 19703796 discloses a selective ammonia sensor, whose loss resistance and capacitance change as a function of the gas concentration in the range of 20 Hz to 1 MHz. German patent documents DE 19756891, DE 19744316, EP 0498916 and DE 4324659 disclose titanate-based oxygen sensors, whose d.c. resistance at several hundred degrees Celsius depends on the oxygen partial pressure of the surrounding gas. Even German patent document DE-3723051 describes such sensors.

An HC sensor, which comprises two resistive oxygen sensors and is also produced using planar technology, is disclosed in German patent document DE 4228052. A typical, planar limiting current sensor for measuring the oxygen content and other components of a gas, is described in Götz R., Rohlf L., Mayer R., Rösch M., Göpel W.: Amperometric Multielectrode Sensor for NOx and Hydrocarbons: Numerical Optimization of operation Parameters and Cell Geometries. Proceedings to "sensor 99", May 18–20, 1999, Nurnberg, pp. 137–142. A gas sensor which utilizes thermoelectric voltage as the measuring effect, and the necessary electrode arrangement, are described in German patent document DE 19853595.

Since such sensors are operated at several hundred degrees Celsius, they must be heated. However, the insulating properties of the substrates that are used are no longer optimal at these temperatures and as a result, the measured variable is affected by the coupling of the voltages required to heat the sensor.

This disadvantage will be explained in the following three examples.

EXAMPLE 1

The sensor is operated at a d.c. voltage $U_0$. In this case a potential distribution, as depicted in FIG. 2, is applied to the sensor heating arrangement 4 on the sensor bottom side. $U_0$=10 V was chosen as an example in FIG. 2. Owing to the electrostatic field distribution, a voltage, which can be measured as the voltage $U_k$ between the electrodes on the sensor upper side, is induced on the sensor upper side. In an equivalent electric circuit one must imagine an ideal voltage source that delivers the voltage $U_k$, with a resistor (the internal resistance of the voltage source) connected in series. Said resistance depends on the dielectric constant and the d.c. insulation resistance of the substrate. Of course, the amount of the voltage $U_k$ also depends on the electrode arrangement (electrode spacing, electrode width, direction of the electrode, etc.), the arrangement of the heating resistors and the substrate thickness. Correspondingly a voltage $U_k$, which renders the measurement of the measured variable difficult, is measured over the electrodes. This voltage is defined as the bias voltage, which can also lead to a change in the functional layer and thus to a falsification of the measurement signal. When this voltage is applied for a prolonged period of time, it can also result in a drift in the measured variable.

EXAMPLE 2

The sensor is operated on alternating voltage with the amplitude $U_0$ at the frequency $f_0$. In this case the description under example 1 is also applicable. The situation is complicated by the fact that the electric insulation resistance of a typical substrate decreases with the frequency. For a commercially available $Al_2O_3$ substrate for thick film technology (96% purity, specific d.c. volume resistance $>10^{10}$ 3 m) the behavior of the specific, i.e. volume resistance $, corrected for geometric influences, is plotted as a function of the temperature T and the measuring frequency f in FIG. 3. It is easy to recognize that precisely in the range of high temperatures and high frequencies the insulation resistance decreases drastically. In such a case the alternating voltage of the heating arrangement is coupled through the substrate, and is in the same phase over the measuring electrodes.

In the case of a sensor that measures the EMF between two electrodes, the coupled alternating voltage will overlay the EMF and will falsify the measured variable. For this case FIG. 4 depicts an equivalent electric circuit. As a function of the dielectric constant and the thickness of the substrate, resulting from the substrate capacitance, labeled as $C_{substrate}$, there is, in addition to the coupling denoted by the ohmic loss resistance $R_{substrate}$, also a capacitive coupling, which is out of phase by 90 degrees and can be measured at the electrodes. The capacitive coupling takes place over the capacitive voltage divider $C_{substrate}$-$C_{internal}$, where $C_{internal}$ reflects the capacitive resistance and $R_{internal}$ reflects the internal resistance of the sensor.

In the case of highly resistive functional layers with low capacitance, where the minimum capacitance change must be measured in the pF (=pico-farad) range, as presented in the DE 19635977 or the EP 0426989, the coupled alternating voltage can have a significant effect on the finding of the measured variable.

EXAMPLE 3

The sensor is operated by means of a constant, but pulsed direct voltage $U_0$ at variable pulse width. Since it is the most energy efficient, it is probably the most common operating mode for a gas sensor, because only the two voltage states $U_0$ and approx. 0 V are applied to the sensor heater, and there is virtually no loss of power over a series resistance. In this case a combination of the effects, described in the examples 1 and 2, occurs. At the instant that the heating process starts, $U_0$ is applied; and the description under example 1 applies. Due to the steep edges, during the turn on and turn off process there are many frequencies in the spectrum. These frequencies are perceived on the sensor upper side in the form of interferences and make it more complicated to determine the measured variable, falsify the findings, or even render it impossible to determine the measured variable.

The object of the invention is to overcome the aforementioned drawbacks of the known gas sensors.

This and other objects and advantages are achieved by the gas sensor according to the invention, in which an electrically, highly conductive (in particular, metallic) shielding structure is disposed between the heating arrangement and the sensor unit, the latter comprising a functional layer and an electrode structure. The shielding structure can comprise, for example, a closed layer. Similarly a network-shaped design or a structure in the form of a line pattern, for example, several parallel conducting tracks, is possible.

A suitable material for the shielding structure is a precious metal, such as platinum (Pt) or gold (Au) or a Pd/Ag alloy, while ceramic materials, such as $Al_2O_3$, MgO or AlN, can be used as the substrate materials. The functional layer of the sensor unit can be made, e.g., of zirconium oxide, a titanate, a zeolite or $\beta$"—$Al_2O_3$.

The sensor unit can be designed such that the complex impedance of the functional layer or the derived variables serve as the measured variable. In addition, the measured variable of the sensor can be an electromotive force, a thermoelectric voltage or an electric current.

Other objects, advantages and novel features of the present invention will become apparent from the following detailed description of the invention then considered in conjunction with the accompanying drawings.

DETAILED DESCRIPTION OF THE DRAWINGS

Figure 1:
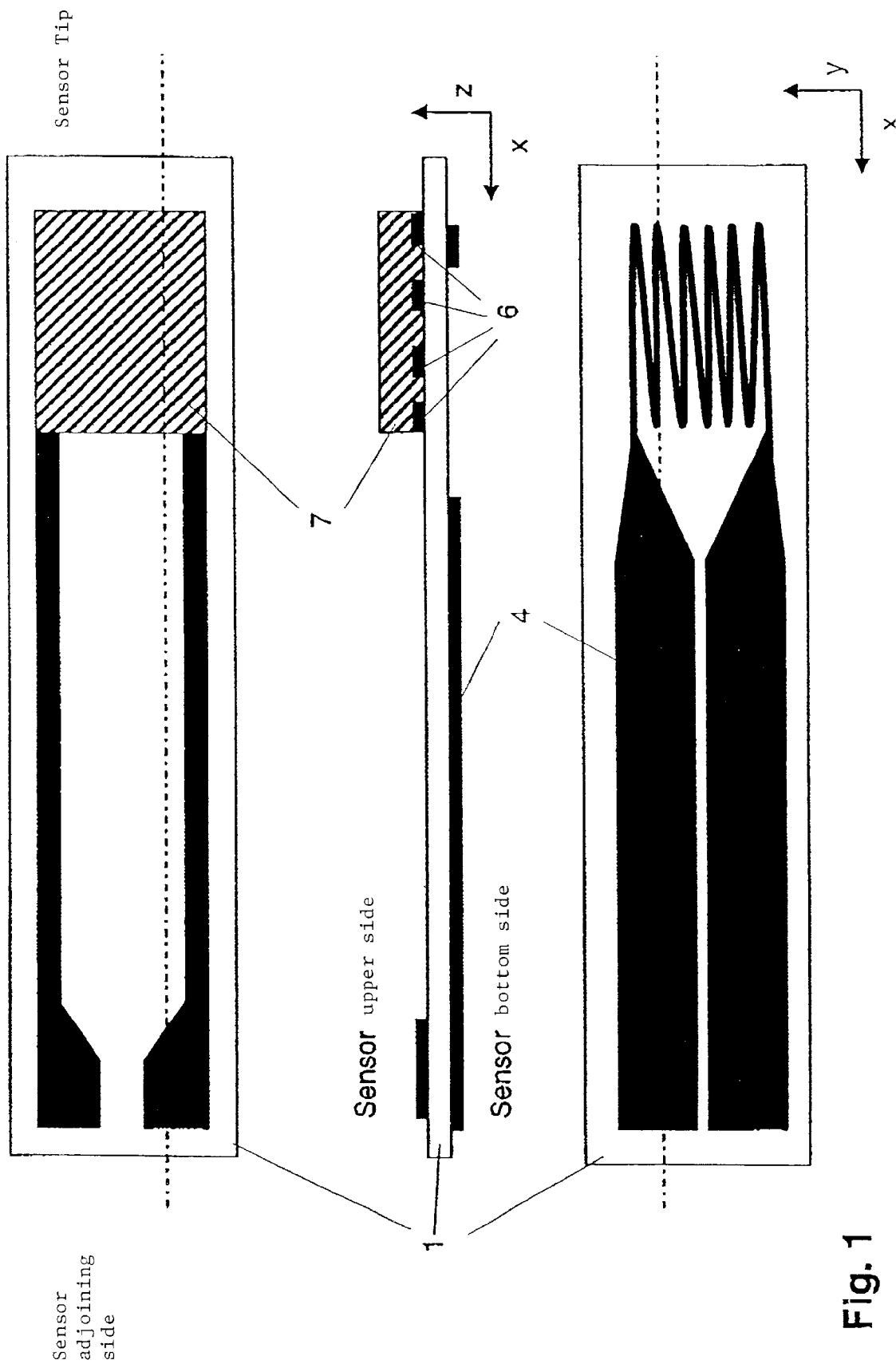
FIG. 1 depicts a known gas sensor, as explained in the introductory part of the specification.
Figure 2:
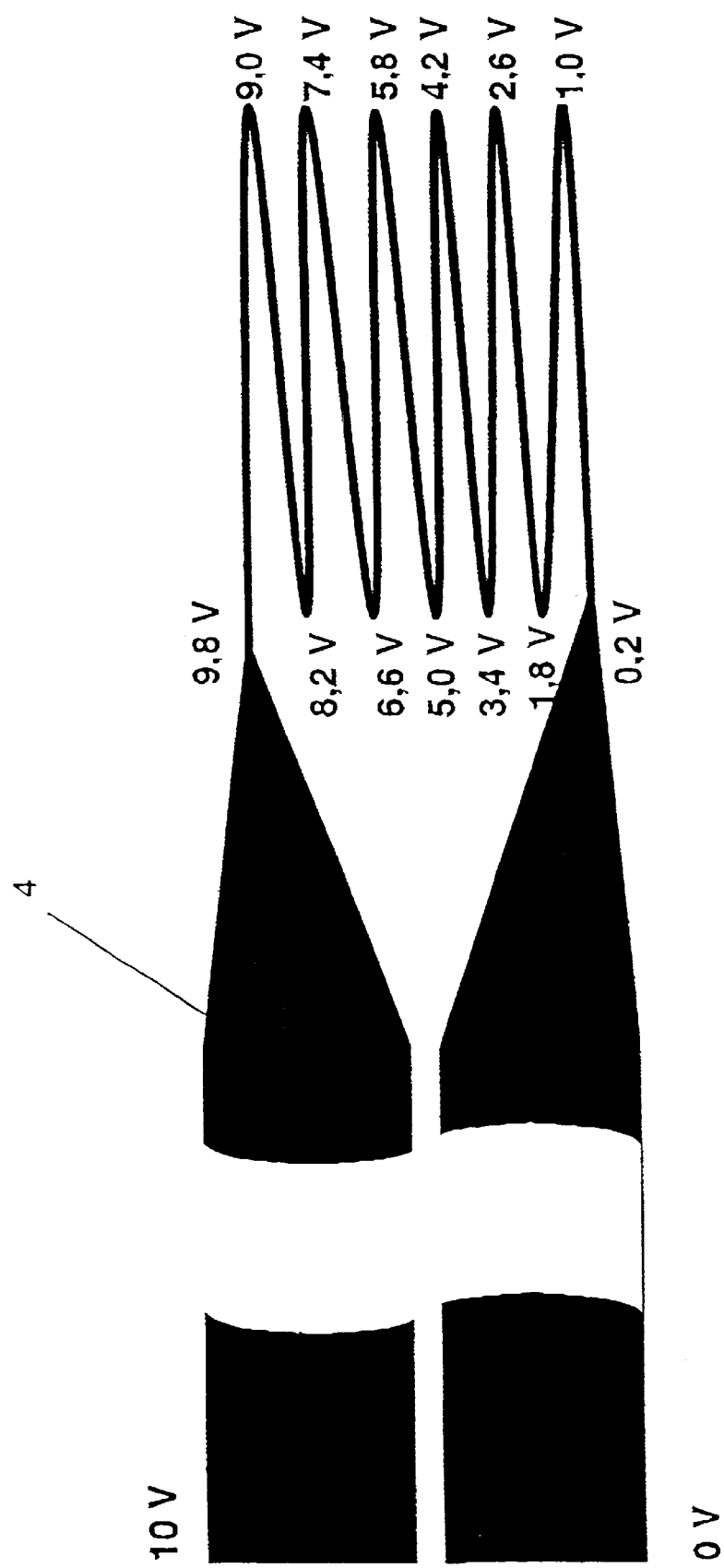
FIG. 2 depicts the voltage curve at the heating arrangement of the gas sensor, according to FIG. 1.
Figure 3:
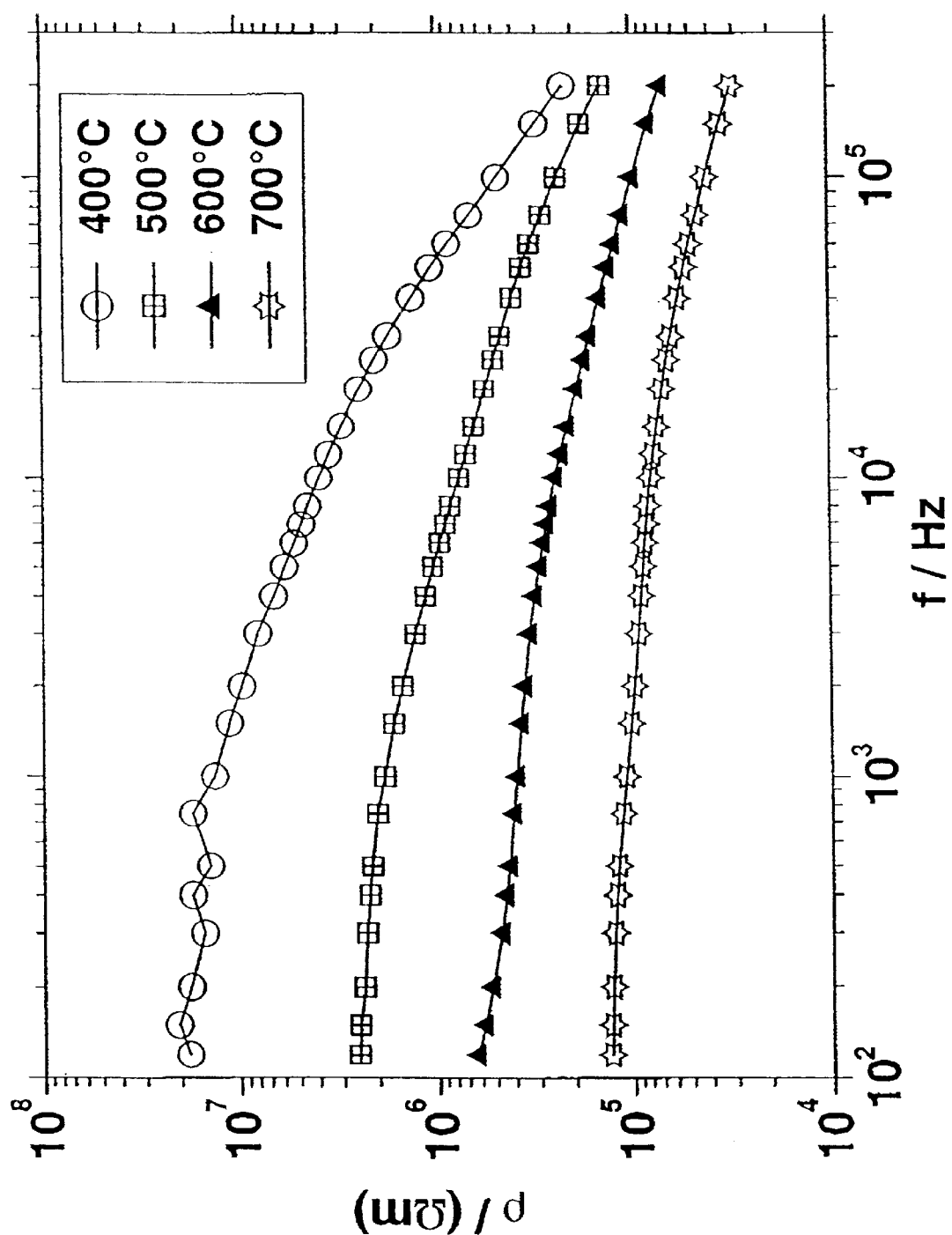
FIG. 3 depicts the specific volume resistance p of a substrate material as a function of the temperature T and the measuring frequency f.
Figure 4:
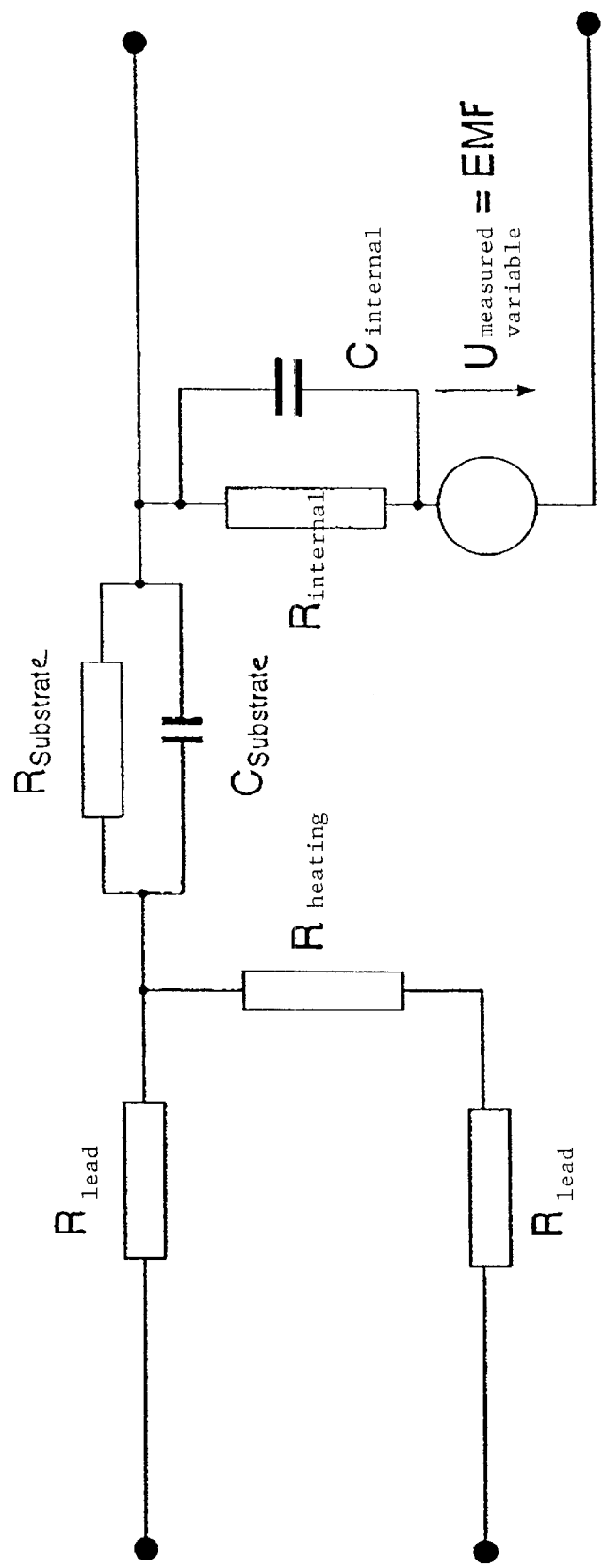
FIG. 4 depicts an equivalent electric circuit of a gas sensor, according to FIG. 1.

A typical structure of a gas sensor, according to the invention, is shown schematically in FIG. 5 and can be produced, for example, as described in the following. In this case the shielding structure of the invention is produced according to thick film technology. However, other technologies can also be used to produce the layer: for example, thin film technologies, such as sputtering, vapor deposition or CVD (=chemical vapor deposition); electrodeposit or other methods.

As customary for thick film technology, a shielding structure 2, (made, for example, of Pt) using thick film technology, is applied on a substrate 1, made, for example, of $Al_2O_3$, and burned in at 1,250° C. In this example the shielding structure is made as a closed layer. The next layer constitutes an insulating layer 3, made, for example, of $Al_2O_3$, which is also applied using thick film technology, but is burned in at 1,200° C. The insulating layer serves to electrically insulate the shielding layer 2 against the electric heating arrangement 4, which is (also made, for example, of Pt), applied using thick film technology and burned in at 1,150° C. Thereafter, the heating arrangement 4 can still be provided, if desired, with a protective layer 5, which can be burned in at 1,100° C. Such a protective layer can be made, e.g., of an electrically insulating glass ceramic. In the next production step, the desired electrode structure 6, made, for example, of gold, is applied by means of thick film technology on the other, still virgin side of the substrate 1 and fired at 950° C. The electrode structure can be designed, e.g., as an interdigitated structure. Depending on the measured variable, however, two single electrodes can also be used. The functional layer 7 is then fired as the last layer at 850° C. With the multilayer construction, shown in FIG. 5, the targeted shielding effect of the invention is obtained.

In another example of the invention, depicted in the graph in FIG. 6, the shielding layer 2 is located on the sensor upper side, directly below the electrode structure 6. Thus, it offers the possibility of starting with the sensor underside during the production phase of the sensor. Then the sequence of production is: substrate 1, heating arrangement 4 (Pt, firing temperature 1,150° C.), protective layer 5 (glass ceramic, 1,100° C.). The production continues on the sensor upper side: shielding layer 2 (gold, 950° C.), insulating layer 3 (low sintering glass ceramic, 925° C.) electrode structure 6 (gold, 900° C.) and finally the functional layer 7 (850° C.).

Figure 5:
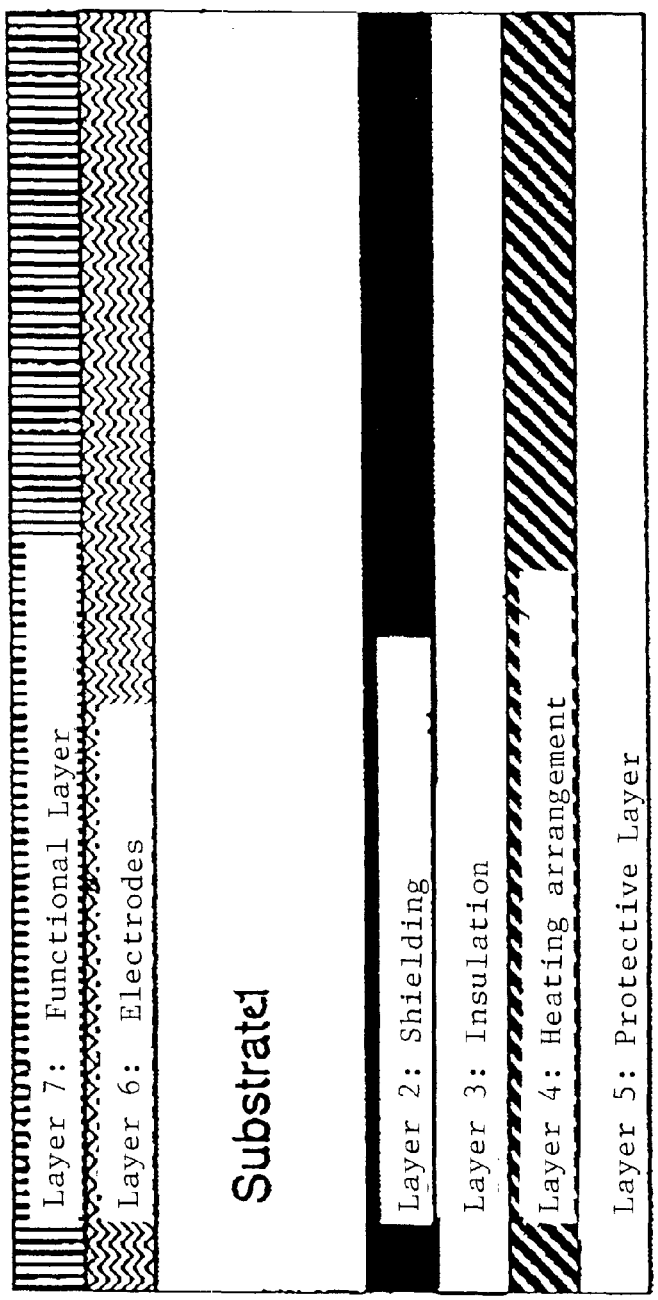
FIGS. 5 to 8 depict respective embodiments of the gas sensor according to the invention.
Figure 6:
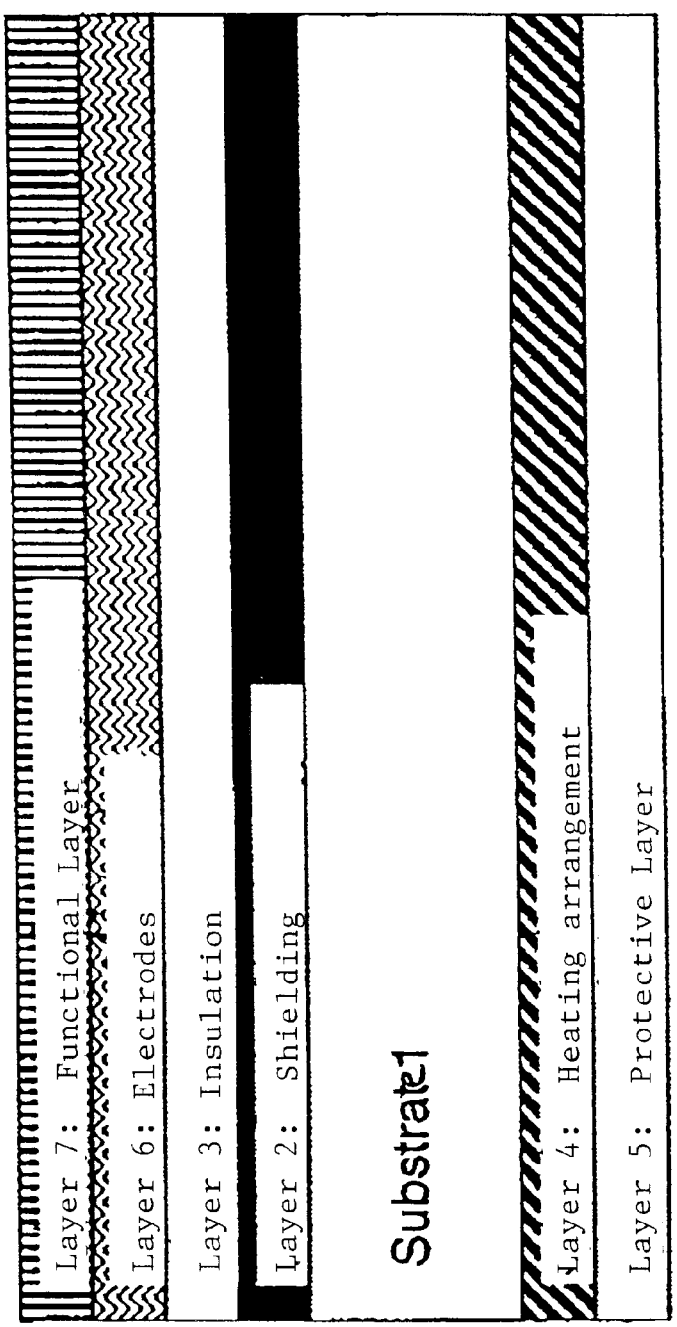

The possible layout options and firing temperatures, as illustrated in FIG. 5 and FIG. 6, are to be regarded only as examples.

Figure 7:
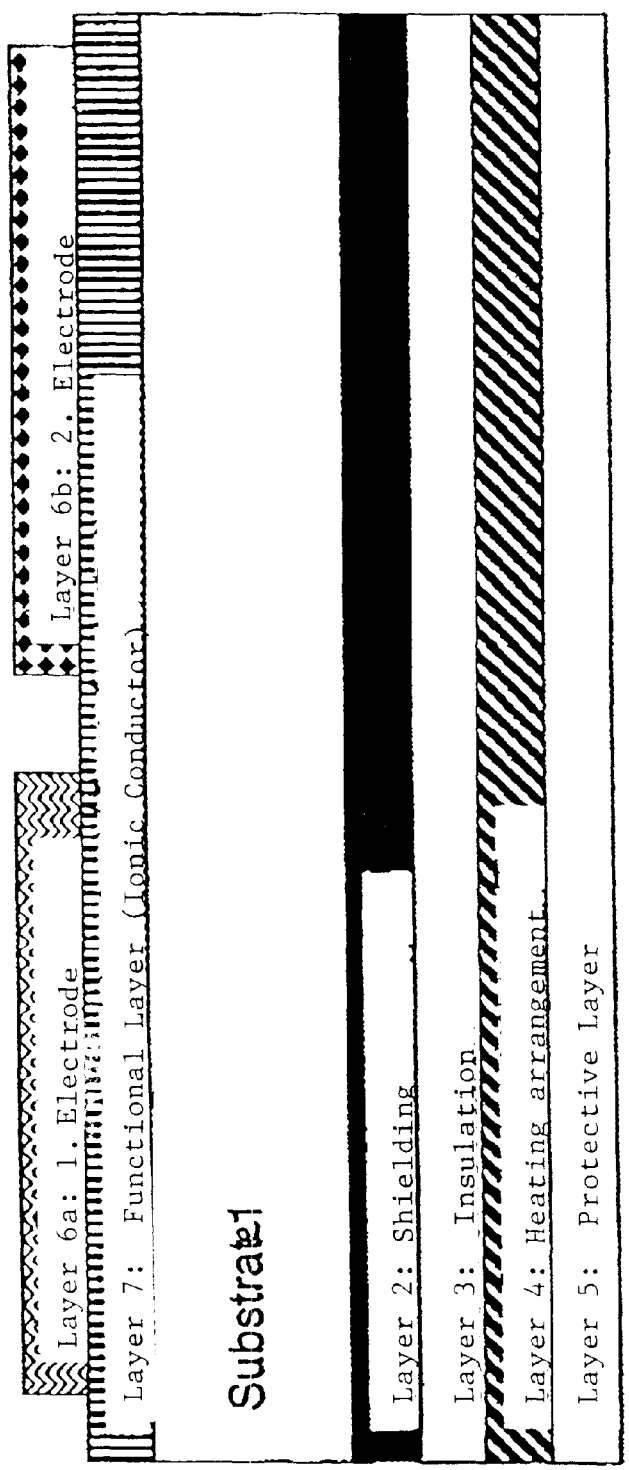

Similarly it is also possible to apply suitable shielding structures below the high sintering functional layers (made, e.g., of titanate or zirconium oxide) through the use of a shielding structure made of Pt and a high sintering $Al_2O_3$ layer as the insulating layer. FIG. 7 is a graphic representation of such an inventive build-up by means of a mix potential sensor, where the electromotive force between two electrodes 6a, 6b (which are made of different materials and which are connected by means of an ionic conductor 7 as the functional layer) is measured. Such sensors are quite suitable for detecting combustible gases. The individual layers are applied in the following order of sequence:

substrate 1 shielding structure 2 insulating layer 3 heating arrangement 4 protective layer 5 functional layer 7 electrodes 6a, 6b.

Figure 8:
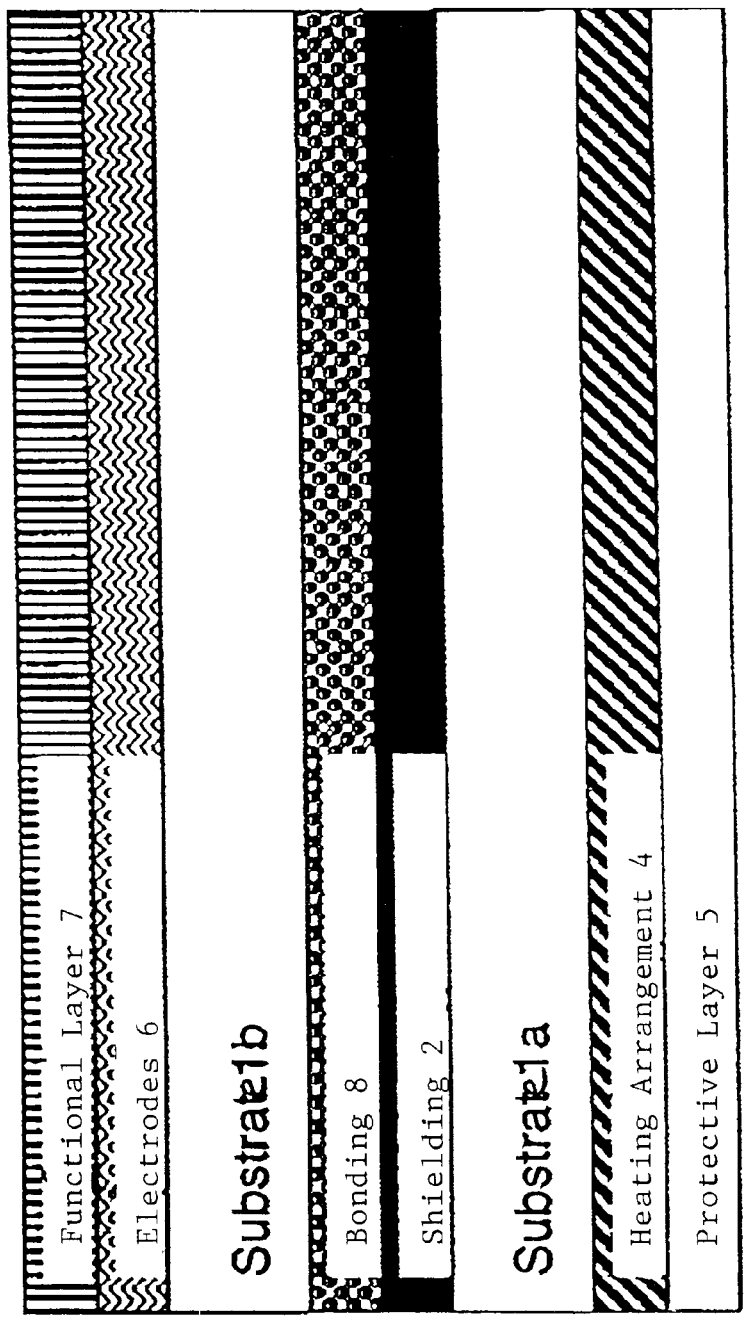

FIG. 8 is a graphic representation of another embodiment of the invention, in which the sensor comprises two partial substrates 1a, 1b. The upper side of the substrate 1a exhibits the shielding layer 2; the bottom side of the substrate exhibits a heating arrangement 4. The upper side of the substrate 1b has an electrode arrangement 6 and a functional layer 7; the bottom side has a ceramic adhesive layer 8. The substrates 1a, 1b, layered in such a manner, are placed one on top of the other. At raised temperature the ceramic adhesive melts (some also harden at room temperature), and the two substrates are then permanently connected together. Of course, the shielding layer can also be located on the underside of the substrate 1b instead of on the top side. For both partial substrates the aforementioned materials for a single substrate can be used.

Another possible form of production lies in the manufacture of such constructional build-ups using multilayer technology. To this end, so-called green tapes are imprinted with metal layers, pressed (laminated) and then sintered together. It is quite feasible to produce all or at least several layers in one firing step by means of so-called co-firing.

It is also regarded as part of the invention to make the shielding structure as a network-like structure rather than a continuous metal layer. The result is not only a saving in precious metal but also an elimination of the delamination problem, which occurs when a metallic layer with a high thermal coefficient of expansion is applied completely over the entire area of an insulating layer having a lower thermal coefficient of expansion.

Instead of a net structure, the shielding structure can also be applied as a line structure.

The electrode structure can be designed, e.g., as an interdigitated structure. However, two individual electrodes or a four conductor arrangement can also be applied. Of course, the electrode arrangements, described in the passages of the literature cited in the introductory part of the specification, can also be used.

FIGS. 9–12 depict measurement graphs that demonstrate the positive effect of the inventive gas sensor in a practical application.

Figure 9:
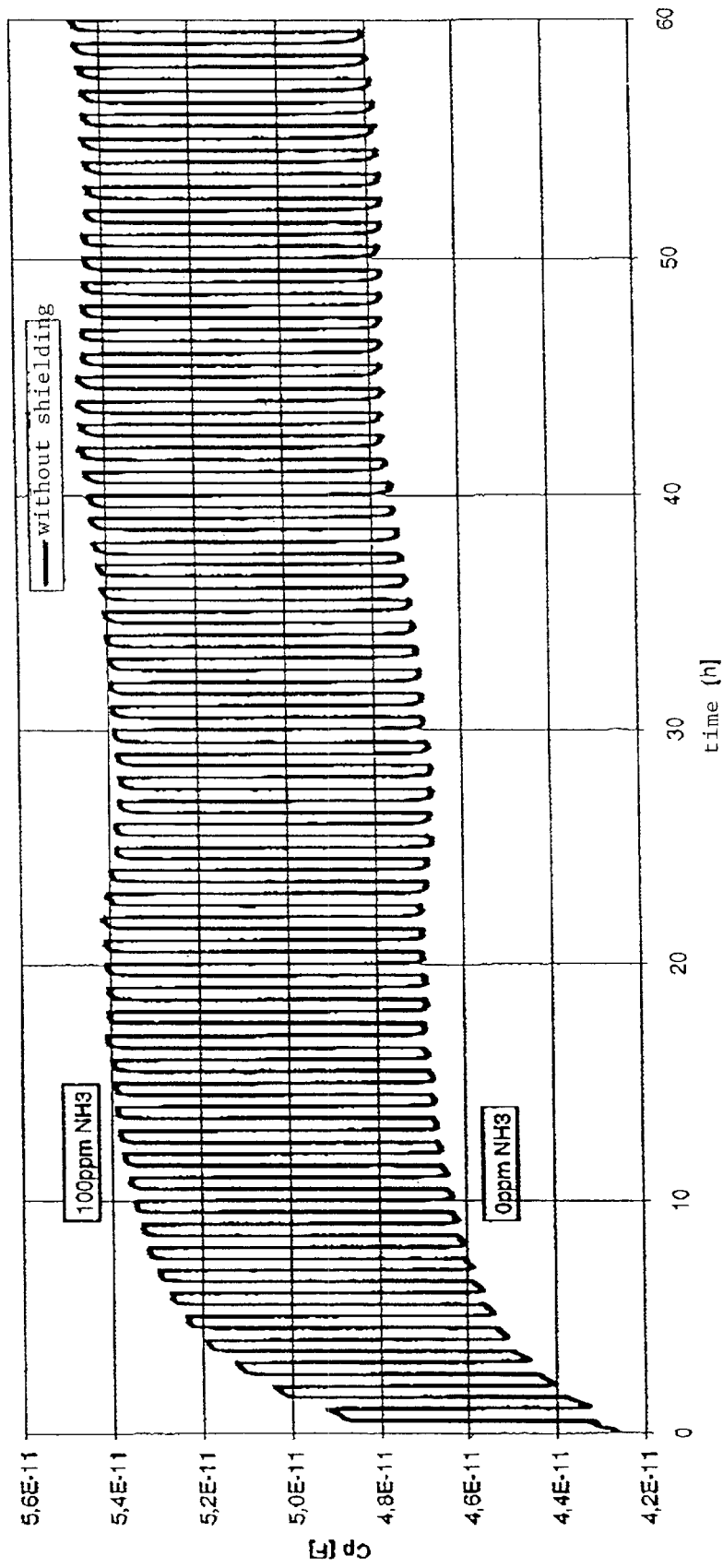
FIGS. 9 to 12 are measurement graphs, recorded with a gas sensor (FIGS. 10, 12) of the invention for comparison with the measurement graphs, recorded with a known gas sensor (FIGS. 9, 11).

FIG. 9 depicts the measurement curve of a gas sensor produced according to European patent document EP 0426989, without the shielding structure of the invention. The measurement curve shows the behavior of the capacitance of the sensor over time during reciprocal testing with 0 and 100 ppm of the test gas ammonia over time. One can see that the sensor signal drifts and that the sensor signal is also blanketed by a beat-like interference. In addition, as time advances, the signal deviation decreases.

Figure 10:
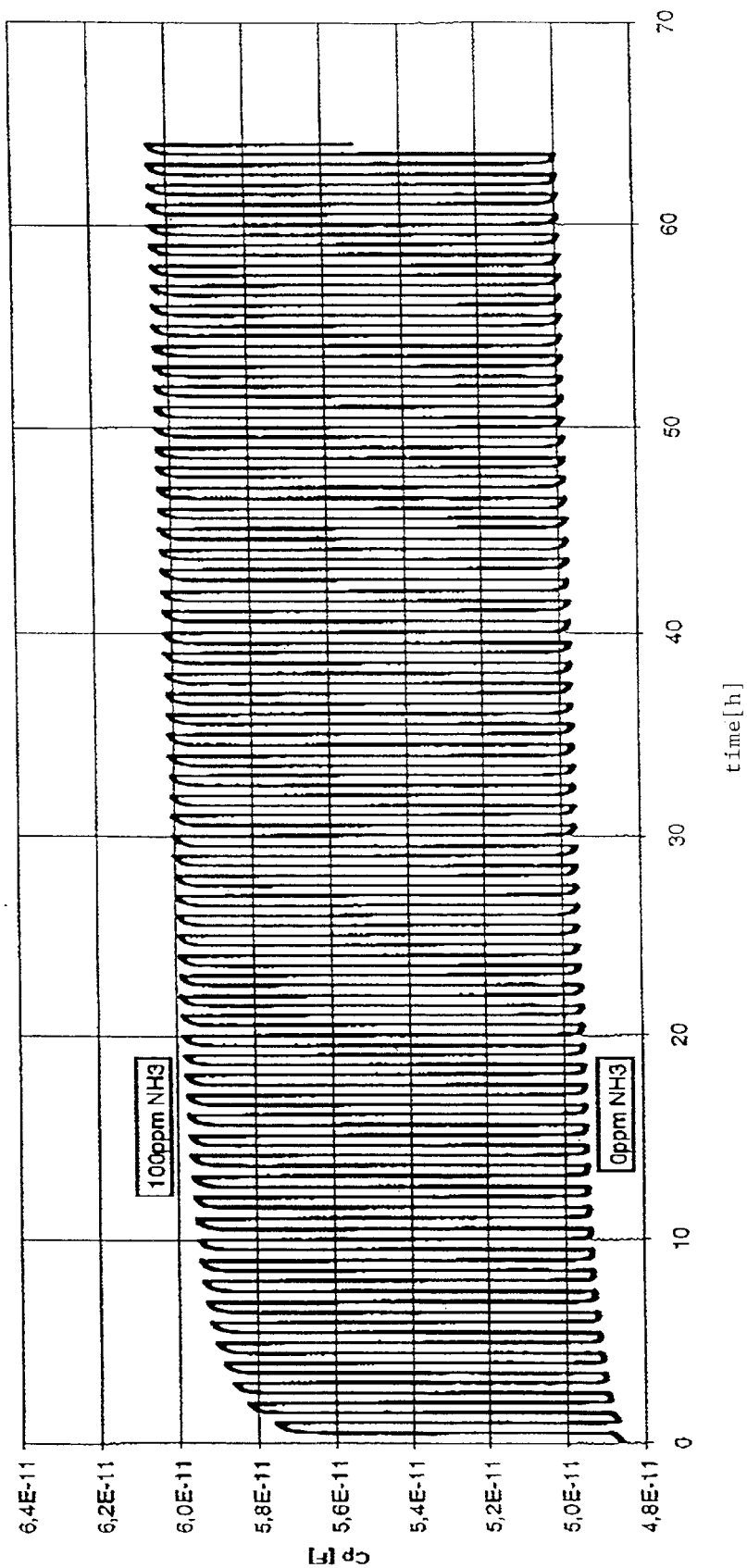

FIG. 10 shows the measurement curve, recorded with a sensor, which is produced identically with that of FIG. 9, with the sole exception that the sensor was produced with an electrical shielding layer, as described above. Now one can barely recognize a sensor drift, and the sensor deviation also remains unchanged over longer periods of time.

Figure 11:
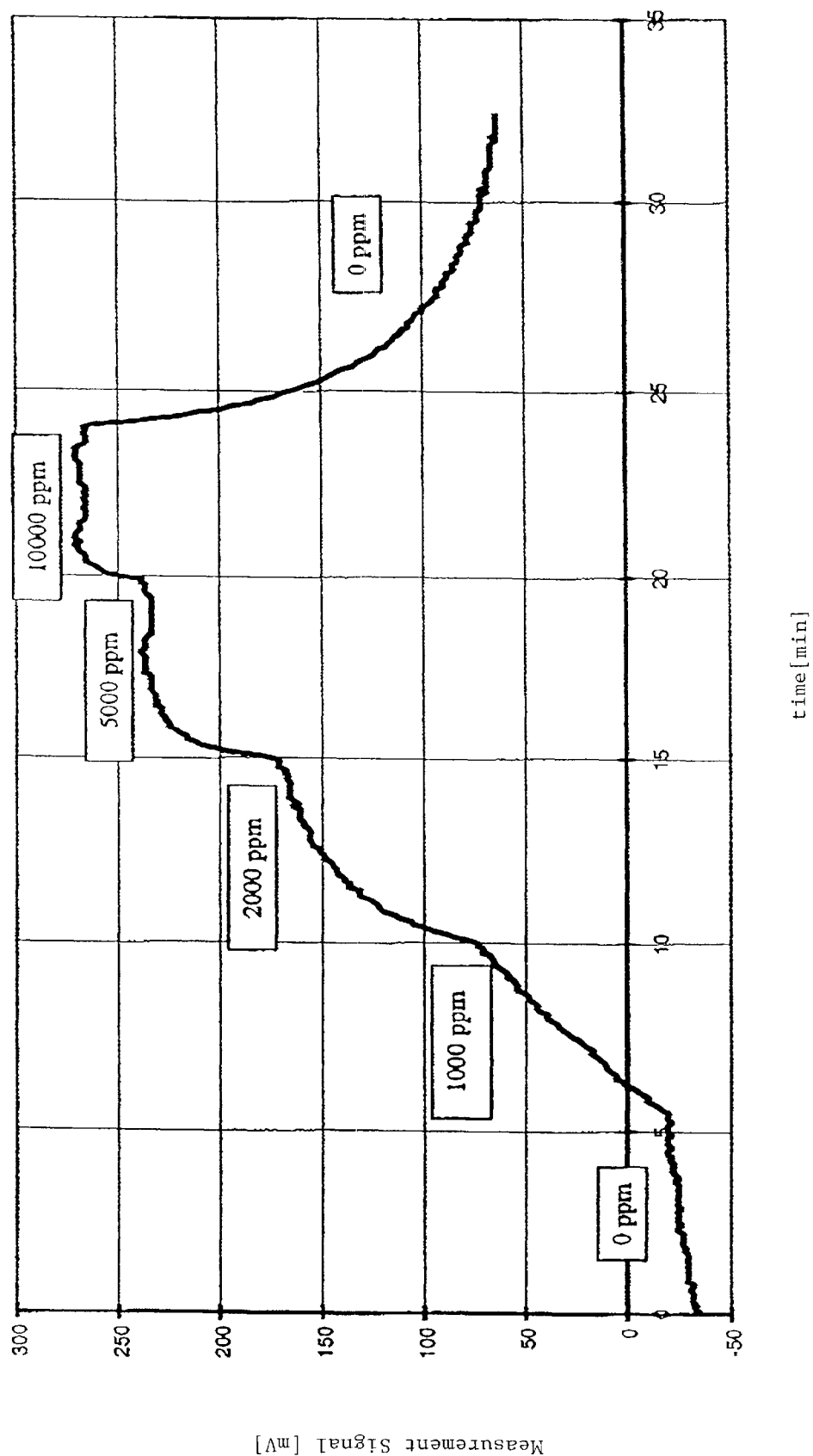

FIG. 11 shows the measurement curve of a sensor for a combustible gas, whose concentration in the gas was changed suddenly every 5 minutes. The corresponding concentrations are indicated respectively. The sensor was produced according to the example in FIG. 7, but without the shielding layer. One perceives a severe drift of the zero line of the sensor signal. In addition, the sensor signal is blanketed by interferences.

Figure 12:
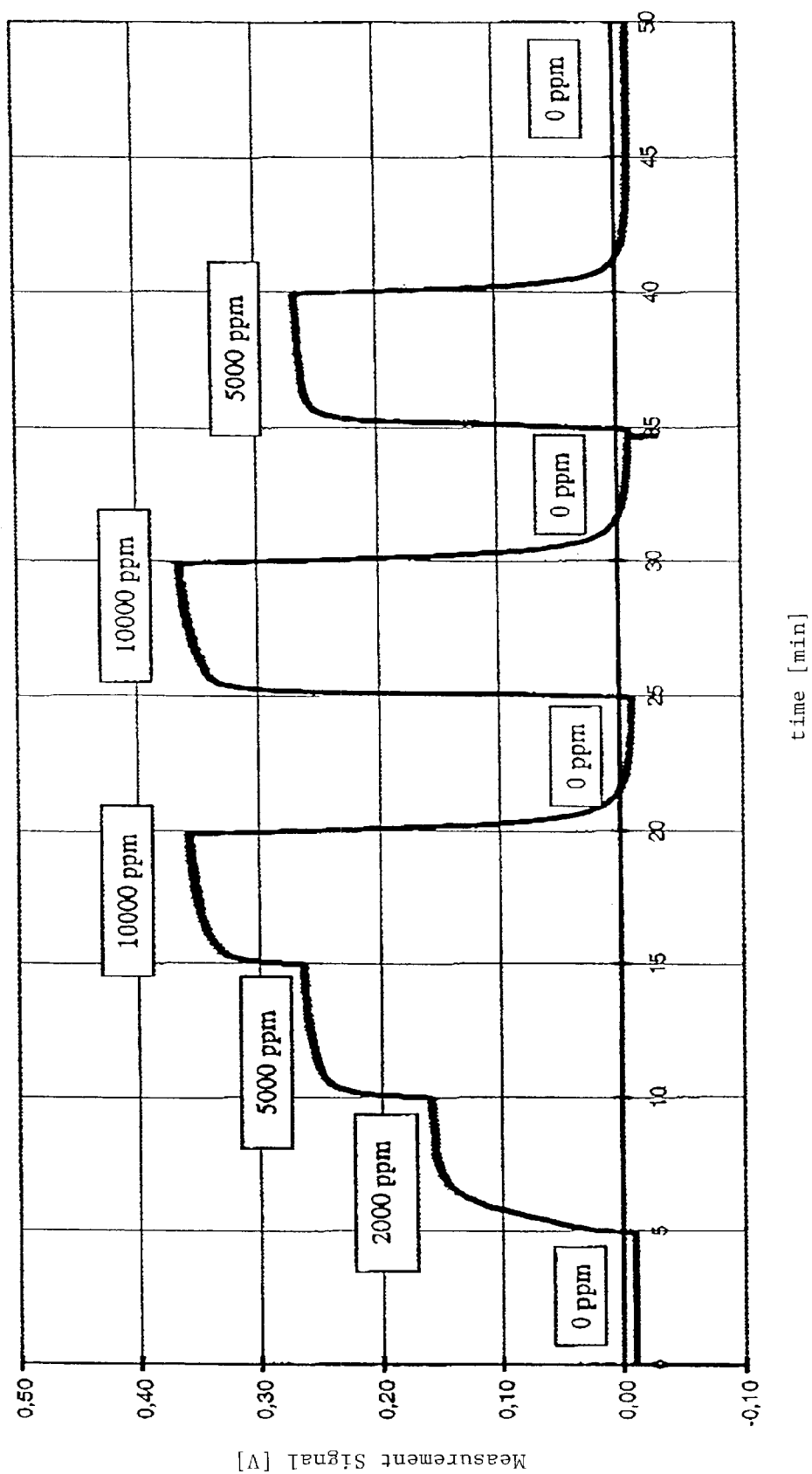

FIG. 12 shows the behavior of an identical sensor, but with the shielding layer of the invention. It is clear that the sensor zero line is maintained over time. There is no drifting of the signal. Furthermore, one can hardly recognize any more an overlaying of interfering signals.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A gas sensor, comprising:

a substrate;

a sensor unit, comprising a functional layer and an electrode structure;

an electric heating arrangement for heating the sensor; and an electrically conductive shielding structure disposed between the sensor unit and the electric heating arrangement, to shield the measurement process at the sensor unit from interferences owing to said heating;

wherein the substrate comprises at least two partial substrates, with the shielding structure disposed therebetween.

2. The gas sensor according to claim 1, wherein the sensor unit and the heating arrangement are disposed on opposite sides of the substrate.

3. The gas sensor according to claim 2, wherein the shielding structure is disposed between the substrate and the heating arrangement.

4. The gas sensor according to claim 2, wherein the shielding structure is disposed between the substrate and the sensor unit.

5. The gas sensor according to claim 1, wherein the shielding structure is one of a closed layer, network-shaped, and a line pattern.

6. The gas sensor according to claim 1, wherein the shielding structure is made of a precious metal.

7. The gas sensor according to claim 1, wherein the substrate is made of a ceramic material.

8. The gas sensor according to claim 7, wherein the ceramic material is selected from the group consisting of $Al_2O_3$, MgO and AlN.

9. A gas sensor, comprising:

a substrate;

a sensor unit, comprising a functional layer and an electrode structure;

an electric heating arrangement for heating the sensor; and an electrically conductive shielding structure disposed between the sensor unit and the electric heating arrangement, to shield the measurement process at the sensor unit from interferences owing to said heating;

wherein the functional layer of the sensor unit is made of a material selected from the group consisting of zirconium oxide, a titanate, a zeolite, and β" $Al_2O_3$.

10. A gas sensor, comprising:

a substrate;

a sensor unit, comprising a functional layer and an electrode structure;

an electric heating arrangement for heating the sensor; and an electrically conductive shielding structure disposed between the sensor unit and the electric heating arrangement, to shield the measurement process at the sensor unit from interferences owing to said heating;

wherein the measured variable, measured at the sensor unit, is one of complex impedance and a measured variable derived from complex impedance.

11. The gas sensor according to claim 1, wherein the sensor unit, is one of electromotive force, thermoelectric voltage and electric current.

12. The gas sensor according to claim 1, wherein it is produced using one of thick film technology, thin film technology and a combination of both methods.

* * * * *